US010610148B2

(12) United States Patent
Girouard et al.

(10) Patent No.: US 10,610,148 B2
(45) Date of Patent: Apr. 7, 2020

(54) METHOD OF MONITORING A PATIENT FOR SEIZURE ACTIVITY

(71) Applicant: Brain Sentinel, Inc., San Antonio, TX (US)

(72) Inventors: Michael R. Girouard, Shavano Park, TX (US); Luke E. Whitmire, San Antonio, TX (US)

(73) Assignee: Brain Sentinel, Inc., San Antonio, TX (US)

( * ) Notice: Subject to any disclaimer, the term of this patent is extended or adjusted under 35 U.S.C. 154(b) by 161 days.

(21) Appl. No.: 15/567,347

(22) PCT Filed: Apr. 16, 2016

(86) PCT No.: PCT/US2016/028005
§ 371 (c)(1),
(2) Date: Oct. 17, 2017

(87) PCT Pub. No.: WO2016/168777
PCT Pub. Date: Oct. 20, 2016

(65) Prior Publication Data
US 2018/0160964 A1 Jun. 14, 2018

Related U.S. Application Data

(60) Provisional application No. 62/149,434, filed on Apr. 17, 2015.

(51) Int. Cl.
*A61B 5/00* (2006.01)
*A61B 5/04* (2006.01)
(Continued)

(52) U.S. Cl.
CPC ............ *A61B 5/4094* (2013.01); *A61B 5/048* (2013.01); *A61B 5/0488* (2013.01); *A61B 5/726* (2013.01);
(Continued)

(58) Field of Classification Search
None
See application file for complete search history.

(56) References Cited

U.S. PATENT DOCUMENTS 3,815,611 A 6/1974 Denniston, III
4,566,464 A 1/1986 Piccone et al.
(Continued)

FOREIGN PATENT DOCUMENTS

EP 1517298 3/2005
EP 2123221 11/2009
(Continued)

OTHER PUBLICATIONS

Conradsen, et al., "Evaluation of novel algorithm embedded in a wearable sEMG device for seizure detection," 34th Annual International Conference of the IEEE EMBS, San Diego, California, USA, Aug. 28-Sep. 1, 2012, pp. 2048-2051.
(Continued)

*Primary Examiner* — Etsub D Berhanu
(74) *Attorney, Agent, or Firm* — Pizarro Allen PC

(57) ABSTRACT

A method of monitoring a patient for seizure activity may include detecting portions of elevated electromyography signal amplitude and analyzing whether the elevations meet one or characteristics of either an epileptic seizure or non-epileptic psychogenic event.

13 Claims, 9 Drawing Sheets

(51) Int. Cl.
 *A61B 5/0488* (2006.01)
 *A61B 5/048* (2006.01)
(52) U.S. Cl.
 CPC .......... *A61B 5/7257* (2013.01); *A61B 5/7282* (2013.01); *A61B 5/04015* (2013.01)

(56) References Cited

U.S. PATENT DOCUMENTS

| | | |
|---|---|---|
| 5,263,489 A | 11/1993 | Johnson et al. |
| 5,269,302 A | 12/1993 | Swartz et al. |
| 5,311,876 A | 5/1994 | Olsen et al. |
| 5,349,962 A | 9/1994 | Lockard et al. |
| 5,373,852 A | 12/1994 | Harrison et al. |
| 5,743,860 A | 4/1998 | Hively et al. |
| 5,810,747 A | 9/1998 | Brudny et al. |
| 5,871,517 A | 2/1999 | Abrams et al. |
| 5,995,868 A | 11/1999 | Dorfmeister et al. |
| 6,018,682 A | 1/2000 | Rise |
| 6,238,338 B1 | 5/2001 | DeLuca et al. |
| 6,440,067 B1 | 8/2002 | DeLuca et al. |
| 6,549,804 B1 | 4/2003 | Osorio et al. |
| 6,597,944 B1 | 7/2003 | Hadas |
| 6,643,541 B2 | 11/2003 | Mok et al. |
| 6,678,549 B2 | 1/2004 | Cusimano et al. |
| 6,819,956 B2 | 11/2004 | DiLorenzo |
| 7,188,151 B2 | 3/2007 | Kumar |
| 7,209,787 B2 | 4/2007 | DiLorenzo |
| 7,231,254 B2 | 6/2007 | DiLorenzo |
| 7,242,984 B2 | 7/2007 | DiLorenzo |
| 7,277,758 B2 | 10/2007 | DiLorenzo |
| 7,539,533 B2 | 5/2009 | Tran |
| 8,386,025 B2 | 2/2013 | Hoppe |
| 8,983,591 B2 | 3/2015 | Leininger et al. |
| 9,186,105 B2 | 11/2015 | Leininger et al. |
| 9,439,595 B2 | 9/2016 | Leininger et al. |
| 9,603,573 B2 | 3/2017 | Leininger et al. |
| 9,833,185 B2 | 12/2017 | Leininger et al. |
| 9,949,654 B2 | 4/2018 | Conradsen et al. |
| 10,226,209 B2 | 3/2019 | Girouard et al. |
| 2003/0236474 A1 | 12/2003 | Singh |
| 2004/0131998 A1 | 7/2004 | Marom et al. |
| 2005/0177400 A1 | 8/2005 | Rosenfeld et al. |
| 2005/0197590 A1 | 9/2005 | Osorio et al. |
| 2008/0001735 A1 | 1/2008 | Tran |
| 2008/0005838 A1 | 1/2008 | Wan Fong et al. |
| 2008/0077039 A1 | 3/2008 | Donnett et al. |
| 2009/0137921 A1 | 5/2009 | Kramer et al. |
| 2010/0121213 A1 | 5/2010 | Giftakis et al. |
| 2010/0121215 A1 | 5/2010 | Giftakis et al. |
| 2010/0137735 A1 | 6/2010 | Hoppe |
| 2010/0198098 A1 | 8/2010 | Osorio et al. |
| 2011/0230730 A1* | 9/2011 | Quigg .................. A61B 5/1121 600/301 |
| 2012/0029322 A1 | 2/2012 | Wartena et al. |
| 2012/0029390 A1 | 2/2012 | Colborn |
| 2012/0083700 A1 | 4/2012 | Osorio |
| 2012/0083701 A1 | 4/2012 | Osorio |
| 2012/0108999 A1 | 5/2012 | Leininger et al. |
| 2012/0116183 A1 | 5/2012 | Osorio |
| 2012/0123232 A1 | 5/2012 | Najarian et al. |
| 2012/0197092 A1 | 8/2012 | Luo et al. |
| 2012/0226108 A1 | 9/2012 | Osorio |
| 2012/0283526 A1 | 11/2012 | Gommesen et al. |
| 2012/0310050 A1 | 12/2012 | Osorio |
| 2013/0012830 A1 | 1/2013 | Leininger et al. |
| 2013/0060167 A1 | 3/2013 | Dracup et al. |
| 2013/0095459 A1 | 4/2013 | Tran |
| 2013/0096441 A1 | 4/2013 | Osorio |
| 2013/0116514 A1 | 5/2013 | Kroner et al. |
| 2013/0154827 A1 | 6/2013 | Housley |
| 2013/0281797 A1 | 10/2013 | Sabesan |
| 2014/0163413 A1 | 6/2014 | Conradsen et al. |
| 2014/0275831 A1 | 9/2014 | Osorio |
| 2014/0276181 A1 | 9/2014 | Sun |
| 2014/0276238 A1 | 9/2014 | Osorio |
| 2015/0119746 A1 | 4/2015 | Conradsen |
| 2015/0289824 A1 | 10/2015 | Leininger et al. |
| 2016/0029947 A1 | 2/2016 | Girouard et al. |
| 2016/0166208 A1 | 6/2016 | Girouard et al. |
| 2016/0296156 A1 | 10/2016 | Conradsen et al. |

FOREIGN PATENT DOCUMENTS

| | | |
|---|---|---|
| JP | 2003220046 A | 5/2003 |
| WO | WO9531932 | 11/1995 |
| WO | WO9726823 | 7/1997 |
| WO | WO2009081206 | 7/2009 |
| WO | WO2012051628 | 4/2012 |
| WO | WO2012102974 | 8/2012 |
| WO | WO2013006728 | 1/2013 |
| WO | WO2013185775 | 12/2013 |

OTHER PUBLICATIONS

Conradsen, et al., "Seizure Onset Detection based on a Uni- or Multi-modal Intelligent Seizure Acquisition (UISA/MISA) System," 32nd Annual International Conference of the IEEE EMBS Buenos Aires, Argentina, Aug. 31-Sep. 4, 2010, pp. 3269-3272.

Conradsen, et al., "Dynamics of muscle activation during tonic-clonic seizures," Epilepsy Research, vol. 104, Issues 1-2, Mar. 2013, pp. 84-93.

Sandor Beniczky, et al., "Quantitative analysis of surface electromyography during epileptic and nonepileptic convulsive seizures," Epilepsia, vol. 55, Issue 7, Jul. 2014, pp. 1128-1134.

Rens Wientjes, "Potential Value of Surface Electromyography for Automated Epileptic Seizure Detection for Children in a Home Monitoring System," Eindhoven University of Technology Department of Electrical Engineering Signal Processing Systems, Master of Science Thesis, Project Period May 2006-Aug. 2007, Report 1107, pp. 1-101.

Conradsen, et al., "Patterns of Muscle Activation During Generalized Tonic and Tonic-Clonic Epileptic Seizures," Wiley Periodicals, Inc., 2011 copyright International League Against Epilepsy, pp. 1-8.

Conradsen, et al., "Multi-Modal Intelligent Seizure Acquisition (MISA) System—A New Approach Towards Seizure Detection Based on Full Body Motion Measures," 31st Annual International Conference of the IEEE EMBS Minneapolis, Minnesota, USA, Sep. 2-6, 2009, pp. 2591-2595.

Uri Kramer, et al., "A Novel Portable Seizure Detection Alarm System: Preliminary Results," Journal of Clinical Neurophysiology, vol. 28, No. 1, Feb. 2011, pp. 36-38.

Kris Cuppens, et al., "Detection of Nocturnal Frontal Lobe Seizures in Pediatric Patients by Means of Accelerometers: A First Study," 31st Annual International Conference of the IEEE EMBS, Minneapolis, Minnesota, USA, Sep. 2-6, 2009, pp. 6608-6611.

Karayiannis, N.B., et al. "Detection of pseudosinusoidal epileptic seizure segments in the neonatal EEG by cascading a rule-based algorithm with a neural network," Biomedical Engineering, IEEE Transactions, vol. 53, Issue 4, Apr. 2006, pp. 633-641 (9 Pages).

Dutch Epilepsy Clinics Foundation Automates the Detection and Diagnosis of Epileptic Seizures with Simulink and the Video and Image Processing Blockset, www.mathworks.com, 91399v00 Jun. 2006 (2 pages), Page Accessed, Jun. 2006.

Epilepsy Detector Application, http://www.epdetect.com/index.html (6 pages), Page accessed, Sep. 2009.

"Medpage ST-2; Movement Sensor Epileptic Seizure Monitor Alarm System with Breathing Monitor Alarm," http://wwww.medpage-ltd.com/page65.html (6 pages), Page accessed Sep. 2009.

NeuroVista, http://www.neurovista.com/research.html (1 page), Page accessed, Sep. 2009.

Abdulhamit Subasi, "Automatic Detection of Epileptic Seizure Using Dynamic Fuzzy Neural Networks," http://www.sciencedirect.com; Oct. 4, 2005 (6 pages).

"Standards for Reporting Electromyography Data," Journal of Athletic Training, available at http://www.nata.org/jat/authors/electromyography_data.htm (4 pages). First Published 1996.

(56) References Cited

OTHER PUBLICATIONS

B. Bigland-Ritchie, et al., "Muscle Temperature, Contractile Speed, and Motoneuron Firing Rates During Human Voluntary Contractions," The American Physiological Society 0161-7567/92, 1992, pp. 2457-2461.
B. Bigland-Ritchie, et al., "Conduction Velocity and EMG Power Spectrum Changes in Fatigue of Sustained Maximal Efforts," The American Physiological Society 0161/7567/81/0000-0000, 1981, pp. 1300-1305.
Juliana Lockman, et al., "Detection of Seizure-Like Movements Using a Wrist Accelerometer," Epilepsy & Behavior 20 (2011) 638-641.
Conradsen et al., "Automatic Multi-modal intelligent seizure acquisition (MISA) system for detection of motor seizures from electromyographic data and motion data," Computer Methods and Programs in Biomedicine 107 (2012) 97-110 (14 Pages).
Poh et al., "Convulsive Seizure Detection Using a Wrist-Worn Electrodermal Activity and Accelerometry Biosensor" Epilepsia, 53(5) e93-e97 (2012) (5 Pages).
Jean_Marc Le Caillec, Rene Garello "Comparison of Statistical Indices using Third Order Statistics for Nonlinearity Detection" in Signal Processing, vol. 84, Issue 3, Mar. (2004), pp. 499-525. (26 Pages).
Xue Wang, Yonghong Chen, "Testing for Statistical Significance in Bispectra: A Surrogate Data Approach and Application to Neuroscience" in IEEE Transactions on Biomedical Engineering, vol. 54, No. 11, Nov. 2007, pp. 1974-1982. (9 pages).
A. Dahaba et al. "Bispectral Index (BIS) monitoring of acute encephalitis with refractory, repetitive partial seizures (AERRPS)" in Minerva Anestesiologica, Apr. 2010 pp. 298-201. (4 pages).
K. Chua et al. "Application of higher order statistics/spectra in biomedical signals—A review" in Medical Engineering & Physics vol. 32 Issue 7, Sep. 2010 pp. 679-689. (11 pages).
Muthuswamy et al. "Higher-Order Spectral Analysis of Burst Patterns in EEG" in IEEE Transactions in Biomedical Engineering, vol. 46, No. 1, Jan. 1999. (8 pages).
M.R. James et al. "Pulse Oximetry during apparent tonic-clonic seizures" The Lancet vol. 337 Feb. 16, 1991.
Che-Chang Yang and Yeh-Liang Hsu, "A review of accelerometry-based wearable motion detectors for physical activity monitoring" Medline, vol. 10, No. 8, Aug. 20, 2010 pp. 7772-7788. (17 pages).
Beniczky Sandor et al., "Detection of Generalized tonic-clonic seizures by a wireless wrist accelerometer: A prospective, multi-center center," Epilepsia, vol. 54, No. 4, Feb. 8, 2013 pp. e58-e61 (4 pages).
International Search Report and Written Opinion in PCT/US2012/045609, dated Jan. 25, 2013 (14 Pages).
International Search Report and Written Opinion in PCT/US2014/068246, dated Mar. 2, 2015 (7 Pages).

\* cited by examiner

20

22 — Collecting an electromyography signal and processing the EMG signal to produce EMG signal data 24 — Processing EMG signal data using a Fast Fourier-Transform (FFT) or wavelet transform and isolating EMG signal data associated with one or more frequency bands 26 — Calculating signal magnitudes determined from at least one band that may be active during a clonic phase of a seizure and one or more reference signal magnitudes determined from one or more reference bands 28 — Determining a ratio of signal magnitudes and comparing the ratio to one or more thresholds 30 — Initiating one or more responses

FIG. 2

METHOD OF MONITORING A PATIENT FOR SEIZURE ACTIVITY

CROSS-REFERENCE TO RELATED APPLICATION

This application is a US national stage entry application of International PCT Application No. PCT/US2016/028005 entitled "Method of Monitoring a Patient for Seizure Activity" filed Apr. 16, 2016, which claims priority to U.S. Provisional Patent Application 62/149,434 entitled "Method of Monitoring a Patient for Seizure Activity" filed Apr. 17, 2015, the disclosures of which are hereby entirely incorporated herein by reference.

BACKGROUND

A seizure may be characterized as abnormal or excessive synchronous activity in the brain. At the beginning of a seizure, neurons in the brain may begin to fire at a particular location. As the seizure progresses, this firing of neurons may spread across the brain, and in some cases, many areas of the brain may become engulfed in this activity. Seizure activity in the brain may cause the brain to send electrical signals through the peripheral nervous system to different muscles, the activation of which may produce an electrical signal.

Techniques designed for studying and monitoring seizures have typically relied upon electroencephalography (EEG), which characterizes electrical signals using electrodes attached to the scalp or head region of a seizure-prone individual or seizure patient. In EEG, electrodes may be positioned so as to measure such activity; that is, electrical activity originating from neuronal tissue. Alternatively, electromyography (EMG) may be used for seizure detection. In EMG, an electrode may be placed on or near the skin, over a muscle, to detect electrical signals from muscle fiber activation.

Detecting an epileptic seizure using electroencephalography (EEG) typically requires attaching many electrodes and associated wires to the head and using amplifiers to monitor brainwave activity. The multiple EEG electrodes may be very cumbersome and generally require some technical expertise to apply and monitor. Furthermore, confirming a seizure requires observation in an environment provided with video monitors and video recording equipment. Unless used in a staffed clinical environment, such equipment is frequently not intended to determine if a seizure is in progress, but rather provide a historical record of the seizure after the incident. Such equipment is usually meant for hospital-like environments where a video camera recording or caregiver's observation may provide corroboration of the seizure, and is typically used as part of a more intensive care regimen such as a hospital stay for patients who experience multiple seizures. A hospital stay may be required for diagnostic purposes or to stabilize a patient until suitable medication can be administered. Upon discharge from the hospital, a patient may be sent home often with little further monitoring.

A patient should in some cases be monitored at home for some length of time in case another seizure should occur. While there presently exist ambulatory devices for diagnosis of seizures, they are EEG-based and are generally not designed or suitable for long-term home use or daily wearability. Other seizure alerting systems may operate by detecting motion of the body, usually the extremities. Such systems may generally operate on the assumption that while suffering a seizure, a person will move erratically and violently. For example, accelerometers may be used to detect violent extremity movements. However, depending upon the type of seizure, this assumption may or may not be true. Electrical signals sent from the brain during the seizure are frequently transmitted to many muscles simultaneously, which may result in muscles fighting each other and effectively canceling out violent movement. In other words, the muscles may work to make the person rigid rather than cause actual violent movement. Thus, the seizure may not be consistently detected with accelerometer-based detectors.

Accordingly, there is a need for an epileptic seizure method and apparatus that can be used in a non-institutional or institutional environment without many of the cumbersome electrodes to the head or extremities. Such an apparatus may be minimally intrusive, minimally interfere with daily activities and be comfortably used while sleeping.

SUMMARY

A method of monitoring a patient for seizure activity may include collecting an electromyography signal using one or more electromyography electrodes; sending the electromyography signal to a processor; processing with the processor the collected electromyography signal to identify if the electromyography signal includes elevations in signal amplitude; if elevations in signal amplitude are present, then analyzing if times between said elevations in signal amplitude within a clonic window change in a manner that is typical of a non-epileptic psychogenic event; and if the times between said elevations changes in a manner that is typical of a non-epileptic psychogenic event, then reporting the result to a caregiver.

A method of monitoring a patient for seizure activity may include collecting an electromyography signal using one or more electromyography electrodes; sending the electromyography signal to a processor; processing with the processor the collected electromyography signal to identify if the electromyography signal includes elevations in signal amplitude; if elevations in signal amplitude are present, then analyzing if times between said elevations in signal amplitude within a clonic window change in a manner that is typical of an epileptic seizure; and if the times between said elevations changes in a manner that is typical of an epileptic seizure, then reporting the result to a caregiver.

A method of monitoring a patient for seizure activity may include processing with a processor electromyography signal data to identify if the electromyography signal includes elevations in signal amplitude; if elevations in signal amplitude are present, then analyzing if times between said elevations in signal amplitude within a clonic window change in a manner that is typical of a non-epileptic psychogenic event; and if the times between said elevations changes in a manner that is typical of a non-epileptic psychogenic event, then reporting the result to a caregiver.

BRIEF DESCRIPTION OF THE DRAWINGS

FIG. 2 illustrates embodiments of another method for monitoring a patient for seizure activity.

DETAILED DESCRIPTION

Figure 1:
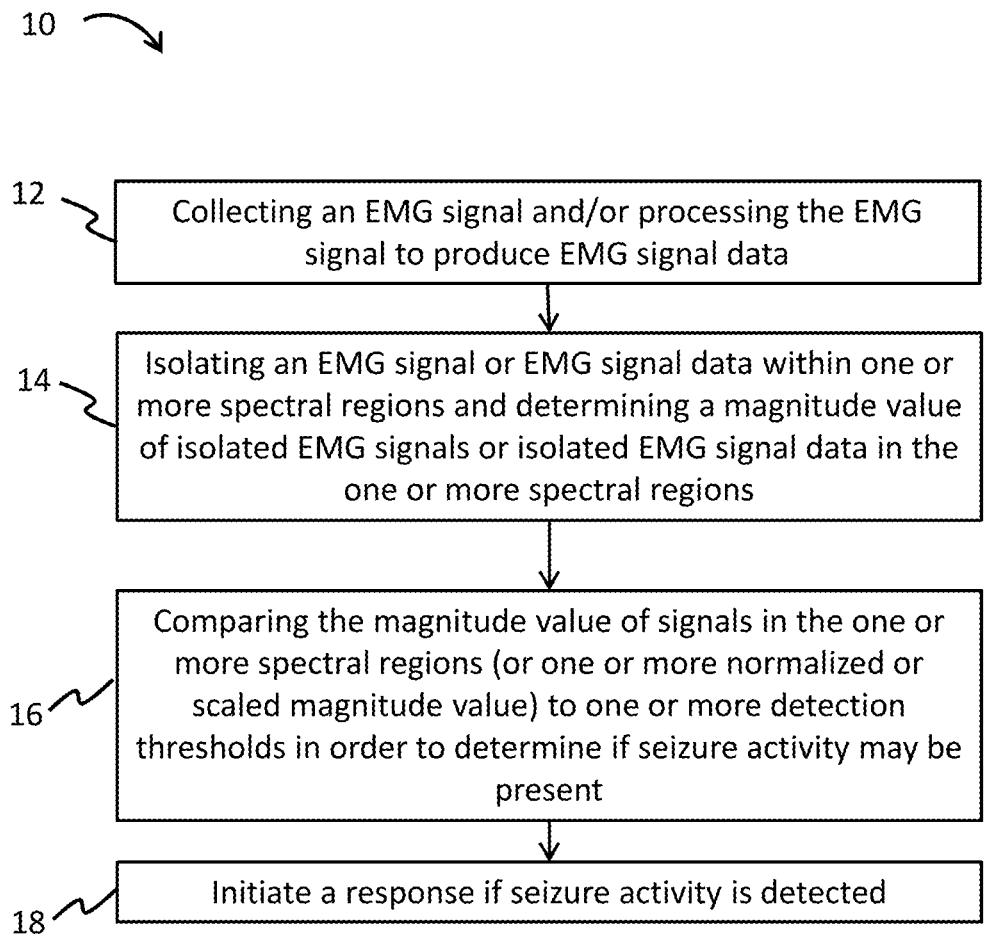
FIG. 1 illustrates embodiments of a method for monitoring a patient for seizure activity.

The following terms as used herein should be understood to have the indicated meanings.

When an item is introduced by "a" or "an," it should be understood to mean one or more of that item.

"Comprises" means includes but is not limited to.

"Comprising" means including but not limited to.

"Computer" means any programmable machine capable of executing machine-readable instructions. A computer may include but is not limited to a general purpose computer, microprocessor, computer server, digital signal processor, or a combination thereof. A computer may comprise one or more processors, which may comprise part of a single machine or multiple machines.

"Computer program" means instructions that may be executed by a computer to cause the computer to operate in a desired manner.

"Computer readable medium" means an article of manufacture having a capacity for storing one or more computer programs, one or more pieces of data, or a combination thereof. A computer readable medium may include but is not limited to a computer memory, hard disk, memory stick, magnetic tape, floppy disk, optical disk (such as a CD or DVD), zip drive, or combination thereof.

"Having" means including but not limited to.

The term "seizure-detection routine" refers to a method or part of a method that may be used to detect seizure activity or to detect activity that may indicate increased risk that a seizure may occur or may have occurred. A seizure-detection routine may be run individually in a strategy for monitoring a patient or may be run in combination with other seizure-detection routines in an overall strategy for patient monitoring.

The apparatuses and methods described herein may be used to detect and characterize seizure events using EMG. In some embodiments, the apparatuses and methods described herein may be configured for real-time monitoring of patients and may be used to timely alert caregivers of seizure events. In other embodiments, methods described herein may be used to characterize stored medical data resulting from EMG monitoring of one or more patients. The apparatuses described herein may include sensors including one or more electrodes disposed on, near, or underneath the skin of a patient (e.g., implanted electrodes may be used with some patients), or attached to a patient's clothing and which may be configured for measurement of muscle electrical activity. In other embodiments, apparatuses and methods described herein may exclude, or exclude use of, a detection sensor, but may include, or include use of, one or more processors suitably configured to receive an EMG signal or EMG signal data and process information encoded therein to detect and characterize seizure or seizure related signals. Detection of seizures is further described in Applicant's U.S. Pat. Nos. 8,983,591 and 9,186,205, Applicant's U.S. patent application Ser. Nos. 13/542,596, 14/816,924, and U.S. Ser. No. 14/920,665, Applicant's International Applications PCT/US14/61783, PCT/US14/68246, and PCT/US15/00475, and Applicant's U.S. Provisional Patent Application Nos. 61/875,429, 61/894,793, 61/910,827, 61/969,660, 61/979,225, 62/001,302, 62/032,147, 62/050,054, and 62/096,331, the disclosures of each of which are herein fully incorporated by reference. Some of the methods described therein may include detection of samples of EMG signal including elevated amplitude over background noise and may include techniques for qualification of samples which may be related to clonic-phase seizure activity. Techniques described therein may further be used to qualify samples related to different parts of the clonic phase. For example, samples may be identified and included in groups encouraging qualification of samples through each of initial, middle, and later portions of the clonic phase. Once qualified, various sample statistics may be determined, tracked over time, and used to better understand a seizure. For example, statistics of samples determined to be qualified-clonic-phase bursts may be used to differentiate a detected seizure for a patient with epilepsy from other seizures resulting from conditions other than epilepsy.

In this disclosure, methods for detecting samples of EMG signal including elevated signal amplitude over background and generating a statistical summary of detected samples are further described. Some of those embodiments may be particularly suited for detection of non-epileptic psychogenic events and differentiating those events from epileptic seizures. In addition, some of the embodiments described herein may be configured for pairing with one or more other seizure-detection routines. Some of those embodiments may be particularly suited for executing high sensitivity detection and classification of seizure activity while also minimizing rates of false detection during patient monitoring.

The elevated portion of a sample may sometimes be referred to as a peak, and in some embodiments, a sample including elevated signal amplitude over background may be detected using one or more peak detection algorithms. For example, some of the peak detection algorithms that may be used in methods described herein may detect peaks by identifying one or more peak edges, including, for example, a leading edge of a peak, a trailing edge of a peak, and/or both leading and trailing edges of a peak.

In some embodiments, samples including elevated signal amplitude over background may be qualified to identify that the samples may properly be associated with the clonic phase of a seizure. For example, qualification may include determining one or more values for one or more properties of a sample or group of samples. Determined property values may further be compared to one or more qualification thresholds. For example, in some embodiments, if a property value of a sample meets a qualification threshold, the sample may be deemed to be qualified and may be referred to as a qualified-clonic-phase burst.

In some embodiments, methods for detection of samples of EMG signal including elevated amplitude over background may include or be executed in combination with one or more routines configured to qualify whether one or more samples may meet one or more qualification criteria or thresholds suitable to identify samples that may be related to seizure activity or a certain part of seizure activity. For example, sample qualification and/or detection routines, examples of which are further described in Applicant's copending U.S. application Ser. No. 14/920,665, may be used in some embodiments described herein to facilitate detection of samples or classification of samples. Some of the aforementioned routines may operate on individual samples including elevated amplitude over background, on groups of samples including elevated amplitude over background, or on both.

In some embodiments, methods for detection of samples of EMG signal including elevated amplitude over background may include or be executed in combination with one or more routines configured to evaluate whether a group of samples may be part of one or more patterns, including, for example, patterns that may be indicative of seizures commonly exhibited by patients with epilepsy or patterns that may be indicative of seizures resulting from conditions other than epilepsy. For example, pattern recognition routines, including, for example, routines further described in Applicant's copending International Application PCT/US15/00475, may be used to search data for one or more patterns and/or qualify samples based on whether samples including elevated amplitude over background may be part of one or more patterns.

Some of the embodiments described herein may be used for tracking changes in muscle activity over time, and may be used for real-time detection of seizure activity. In addition, some embodiments may also be executed as secondary operations to real-time detection. For example, in some embodiments, routines may be used to post-process detected seizures and may be used to organize stored patient medical data. To organize patient data an algorithm may, for example, search patient data, identify instances of seizure or similar activity, and generate statistics of diagnostic value which may be provided to one or more caregivers. For example, seizures of common type or diagnostic significance may be grouped together to further evaluate the efficacy of one or more treatment regimens.

In some embodiments, methods for detection of samples of EMG signal including elevated amplitude over background may include or be executed in combination with one or more other seizure-detection routines. For example, in some embodiments wherein detection of samples of EMG signal including elevated amplitude may be paired with another seizure-detection routine, routines used for sample detection may be selectively executed or organized based on detection of a seizure event. For example, one or more windows of time during which sample statistics may be determined may be set based on detection of seizure activity. In some embodiments, seizure-detection routines may be configured to identify times within the clonic phase of a seizure which may be delayed or offset from the earliest transition times when tonic phase activity may transition into the clonic phase. And, in some embodiments, routines for seizure-detection may identify portions of the clonic phase where detection of samples of EMG signal including elevated amplitude may be made with higher sensitivity.

Generally, detection of a seizure event may indicate a high confidence that a seizure event may be occurring or may have occurred. However, in some embodiments described herein, one or more seizure-detection routines may include or be configured for detection of one or more events which, while showing signs of being associated with a seizure, may or may not indicate the presence of an actual seizure or indicate that a seizure was detected at high confidence. For example, depending on one or more detection thresholds, a seizure-detection routine may be configured to detect one or more parts of an EMG signal that may indicate an increased risk of seizure occurrence, but may be insufficient to fully discriminate signals from some non-seizures sources. Further processing, including, for example, processing to detect and characterize samples of EMG signal including elevated amplitude over background, may then be used to characterize and increase confidence that detected signals should properly be associated with an actual seizure or seizure of a certain type. Alternatively, further processing may sometimes be used to identify that an event thought to be seizure may properly be categorized as associated with a non-seizure event. Accordingly, in some embodiments, processing of collected EMG signal to detect and characterize samples of EMG signal including elevated amplitude over background may be used to reduce rates of incorrect or false positive detections. In some embodiments, further processing of collected EMG signal to detect and characterize samples of EMG signal including elevated amplitude over background may be used to characterize a seizure already detected at high confidence.

FIG. 1 illustrates embodiments of a seizure-detection method 10. In some embodiments, seizure detection method 10 may be configured for high sensitivity detection of the clonic phase of a seizure. And, in some embodiments, seizure-detection method 10 may be paired together with one or more routines configured for detection and classification of samples of EMG signal including elevated signal amplitude over background.

In some embodiments, as shown in a step 12, an EMG signal may be collected using one or more EMG detectors including one or more electrodes. Collecting of an EMG signal may include disposing one or more electrodes in association with one or more muscles of a patient. The electrodes may be suitably configured to transduce energy associated with muscle activation into a form that may be electronically processed. For example, in some embodiments, bipolar differential electrodes may be disposed on the skin of a patient near a patient's biceps, triceps, other patient muscle that may be activated during a seizure, and/or any combination of the muscles thereof.

In some embodiments, detection units may be attached to each of the left and right biceps and/or attached to other suitable muscle pairs on opposite sides of a patient's body. Signals from detectors on opposite sides of a patient's body may be analyzed, and if either of the detectors detects seizure activity, a response may be initiated. In some of those embodiments, signals may further be used to characterize whether seizure activity is symmetrical in strength between the left and right sides of a patient's body or if other asymmetric activity is identified. In some embodiments, a combination of EMG detectors on opposite sides of a patient's body may be used to identify the presence of a complex partial seizure. Detection units and other components of an integrated monitoring system which may be used in some of the embodiments herein are further described in greater detail in the references incorporated herein. For example, a detailed description of embodiments of a monitoring system is included in Applicant's U.S. Pat. No. 8,983,591 which is incorporated herein by reference.

In some embodiments, in step 12, collected EMG signal may further be processed to produce EMG signal data. EMG signal data, as described herein, may refer to collected EMG signal processed to a form suitable for input and use with a computer processor. For example, in some embodiments, a collected EMG signal may be amplified and processed using an analog-to-digital converter in order to produce digital EMG signal data. In some embodiments, other operations, including, for example, rectification, low pass filtering, or other operations which may be used to shape or condition an EMG signal or EMG signal data in ways within the ordinary skill level of a practitioner in the art of EMG signal processing may also be performed in step 12.

In a step 14, EMG signals or EMG signal data may be isolated within one or more spectral regions. In addition, one or more magnitude values for the isolated signals may be determined. A spectral region may also be referred to as a frequency band. In some embodiments, isolation of spectral regions may include collecting time domain EMG signal data and converting the data to the frequency domain using, for example, a Fast Fourier Transform (FFT). For example, in some embodiments, time domain data may be collected for an epoch period of about 0.25 seconds to about 2 seconds (or some other suitable epoch period) and converted to the frequency domain. Epoch periods may sometimes be staggered, such as may be used to reduce latency between seizure occurrence and detection.

In some embodiments, an EMG signal or EMG signal data may be processed by filtering to select one or more frequency bands of various widths. Filtering may be accomplished by software or electronic circuit components, such as bandpass filters (e.g., Baxter-King bandpass filters) suitably weighted. However, such description should not be interpreted as limiting methods herein to filtering using either software or electronic circuit components. For example, in some embodiments, analog or digital signal processing techniques and/or combinations of analog and digital signal processing may be used for isolation of spectral data.

In some embodiments, EMG signals may be isolated in one or more spectral regions including frequencies between about 1 Hz and about 7 Hz. In some embodiments, an EMG signal or EMG signal data may be filtered to isolate one or more spectral regions between a lower frequency boundary, including, for example, a lower frequency boundary of about 0.1 Hz to about 1 Hz. and a higher or cutoff frequency. In some embodiments, the higher frequency cutoff may, for example, be about 60 Hz, about 50 Hz, or about 40 Hz.

Further in the step 14, a magnitude value of isolated signals may be determined. And, in a step 16, one or more magnitude values of isolated signals in one or more spectral regions may be compared to one or more threshold values. For example, if a threshold value is exceeded, seizure activity may be deemed present.

In a step 18, a response to a detection of seizure activity may be made. For example, in some embodiments, a response may include initiating an alarm response. In some embodiments, a detection of seizure activity may include initiating another routine, including, for example, one or more routines designed to detect samples of EMG signal data that may include elevated signal amplitude. In other embodiments, routines designed to identify samples of signal that include elevated signal amplitude may run continuously, and a response to detection of seizure activity in the method 10 may include defining one or more boundaries (e.g., a start time and/or end time) of an analysis window in which various sample statistics are calculated.

FIG. 2 illustrates embodiments of another seizure-detection method 20. Like seizure-detection method 10, seizure-detection method 20 may be configured for high sensitivity detection of the clonic phase of a seizure. And, in some embodiments, seizure-detection method 20 may be paired together with one or more routines configured for detection and classification of samples of EMG signal including elevated signal amplitude over background.

In some embodiments, as shown in a step 22, an EMG signal may be collected using one or more EMG detectors suitably configured with one or more electrodes. Further in step 22, EMG signal may be processed to produce EMG signal data. For example, a collected EMG signal may be amplified and processed using an analog-to-digital converter in order to produce digital EMG signal data. In some embodiments, EMG signal data may then be processed by removing direct current (DC) components of EMG signal data. For example, in some embodiments, a digital first order Infinite Impulse Response (HR) high pass filter may be used to remove a DC offset component. In some embodiments, the DC offset signal may then be rectified and low pass filtered. For example, a double stage exponentially weighted moving average with a smoothing factor of about 0.2 may be used for this purpose. Of course, any suitable smoothing factor may be used. In some embodiments, processing as described herein may limit high frequency components of the EMG signal data to a cutoff frequency of about 40 Hz or may limit high frequency components to some other suitable value.

As shown in a step 24, EMG signal data may then be processed with one or more frequency transforms. For example, the EMG signal data may be transformed to the frequency domain using a Fast Fourier Transform (FFT). In other embodiments, a wavelet transform may be applied to the EMG signal data. For example, a signal may be processed using a Morlet wavelet transform, Haar wavelet transform, Daubechies wavelet transform, harmonic wavelet transform or other suitable wavelet transform. In some embodiments, one or more epoch periods may be selected for use with a frequency transform. That is, data collected within an epoch period may be grouped together and processed using a selected transform. In some embodiments, a transform may include an epoch period of time ranging from about 0.25 seconds to about 2 seconds, for example. In some embodiments, epoch periods may be staggered such as may be used to reduce latency between physical manifestation of seizure activity and detection of seizure activity. Once transformed, components of EMG signal data associated with one or more frequency bands may be isolated for analysis.

As shown in a step 26, one or more signal magnitudes or power contents in two or more frequency bands may be calculated. Calculated magnitudes may be derived from signals isolated within at least one band that may be active during the clonic phase of a seizure. For example, signal magnitude may be calculated for at least one band including frequencies between about 1 Hz and about 7 Hz. Signal magnitudes associated with the aforementioned activity and frequency range may herein be referred to as the detection magnitude (M detection). In addition, a reference magnitude may be calculated for one or more additional frequency bands or reference frequency bands. In some embodiments, one or more reference bands may be used that may be preferentially active during certain parts of the clonic phase. Signal magnitudes calculated from one or more reference frequency band may herein be referred to as a reference magnitude (M reference). In some embodiments, a reference magnitude may be calculated from one or more reference frequency bands including frequencies between about 7 Hz and about 60 Hz, for example. In some embodiments, a lower frequency boundary for a reference band may be about 7 Hz, about 10 Hz, or about 15 Hz, for example. In some embodiments, an upper frequency boundary for a reference band may be about 60 Hz, about 50 Hz, or about 40 Hz, for example.

In some embodiments, one or more ratios of signal magnitude to reference magnitude may be used as indices of seizure activity. For example, as shown in a step 28, a ratio of signal magnitudes may be determined. For example, a ratio of signal magnitudes may be calculated as shown in Equation 1:

$$\text{Detection Ratio} = (M_{detection})/(M_{reference}) \quad \text{Equation 1}$$

Further in step 28, a determined ratio or metric calculated from a determined ratio (e.g., an average detection ratio or smoothed detection ratio) may further be compared to one or more thresholds.

Based on the comparison of a detection ratio to a threshold, as shown in a step 30, one or more system responses may be initiated. For example, in some embodiments, if one or more detection ratios exceeds a threshold value of about 0.5 to about 2.0, it may be deemed that the patient may be experiencing a seizure, and an appropriate response such as execution of one or more alarm protocols may be initiated. In some embodiments, some number of adjacent detection ratios may be averaged together and an average detection ratio value may be compared to a threshold. In some embodiments, an alarm or other response may be initiated if detection ratios associated within some number of adjacent or overlapping epoch periods each achieve a detection ratio that exceeds a threshold. Accordingly, in some embodiments, it may be required that a detection ratio is elevated above a threshold for some duration of time. For example, in some embodiments, a seizure may be detected if detection ratios calculated in at least 4 epoch periods in an 8-period moving window exceed a threshold.

In some embodiments, a response to seizure detection (e.g., using either of the methods 10, 20) may include triggering another analysis routine and/or marking the start of one or more calculation windows associated with that other analysis routine.

Figure 3:
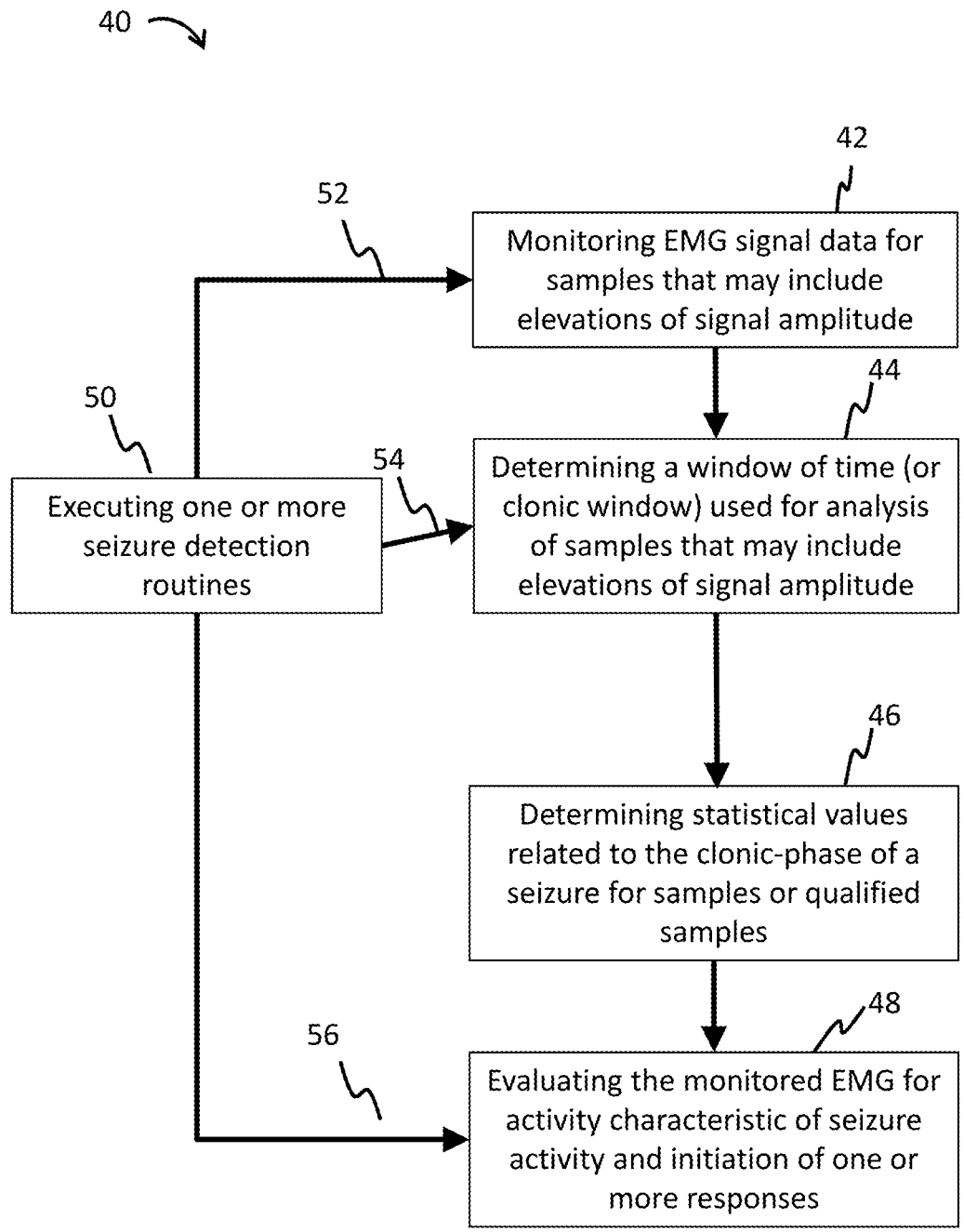
FIG. 3 illustrates embodiments of still another method for monitoring a patient for seizure activity.

FIG. 3 illustrates embodiments of a method 40 for monitoring of a patient for seizure activity. Method 40 may include use of one or more detection routines wherein EMG signals may be monitored for samples of EMG signal data including elevated signal amplitude. In some embodiments, the method 40 may also include use of one or more seizure-detection routines. For example, in some embodiments, method 40 may include use of one or both of the routines 10, 20. In FIG. 3, one or more seizure-detection routines in addition to those described for monitoring of a patient for the presence of samples of EMG signal data including elevated signal amplitude are schematically shown using box 50. In some embodiments, the one or more seizure-detection routines (e.g., routines 10, 20) may communicate with the method 40 in various stages in its operation, as schematically shown in FIG. 3 through the arrows 52, 54, and 56.

As shown in a step 42, EMG signal data may be processed in order to detect samples of EMG signal data including elevated signal amplitude over background. In some embodiments, processing of EMG signal data in step 42 may be executed continuously or periodically throughout a monitoring session for a patient. For example, collected EMG signal data may be processed throughout monitoring using one or more routines which may continuously analyze EMG signal data for samples of EMG signal data which may be elevated over background. In other embodiments, processing of EMG signal data in step 42 may be initiated based on one or more input signals. For example, as shown by the arrow 52, another routine or method (e.g., methods 10, 20) may be configured to provide an input signal suitable to initiate execution of step 42. Therefore, in some embodiments, step 42 may execute selectively in an intermittent or discontinuous manner. In some embodiments, the one or more routines configured to provide an input signal suitable to initiate execution of step 42 may be configured to detect clonic phase seizure activity or a certain part of clonic phase seizure activity, including, for example, parts of clonic phase seizure activity where peak detection may be executed with high sensitivity. For example, in some embodiments, seizure-detection routine 20 may be used to initiate the step 42, and the routine 20 may be calibrated so that routine 20 is executed during time periods which are most suited for high sensitivity detection of peaks.

Still referring to step 42, detection of samples of EMG signal including elevated signal amplitude may include determining an EMG signal amplitude and comparison of the amplitude to a baseline or noise value. In some embodiments, an EMG signal amplitude or EMG signal amplitude above a baseline signal may be scaled in units of noise which may, for example, be set based on a standard deviation measured from a baseline signal. In some embodiments, a baseline signal or noise value may be derived from a previously collected period of EMG signal such as may be obtained during a calibration period or pre-seizure period. For example, in some embodiments, pre-seizure portions of data may be identified based on one or more seizure-detection routines suitably configured to detect a time or time range for the start of seizure activity. For example, either of the routines 10, 20 may be used for this purpose. Once a start time or time range for the start of a seizure is determined, a portion of data that includes one or more pre-seizure time periods may be selected. For example, selection of a pre-seizure portion of data may be based on temporal proximity to a seizure start time. Accordingly, baseline estimates used for baseline correction and noise calculations may be based on pre-seizure time periods that may precede or in some case immediately precede a seizure.

In some embodiments, various operations and/or process techniques may be used as part of a routine executed in the step 42 to monitor an electromyography signal for portions of elevated signal amplitude. For example, in some embodiments, operations such as signal rectification, filtering, isolation of one or more frequency bands of EMG signal, and/or other processing operations may be executed. For example, an analysis protocol may include a peak detection program, which, for example, after band-pass filtering and rectification may identify and shape data. In some embodiments, peak detection may include data smoothing techniques (e.g., moving average filter, Savitzky-Golay filter, Gaussian filter, Kaiser Window, various wavelet transforms, and the like), baseline correction processes (e.g., monotone minimum, linear interpolation, loss normalization, moving average of minima, and the like) and application of one or more peak-finding criteria (SNR, detection/intensity threshold, slopes of peaks, local maximum, shape ratio, ridge lines, model-based criterion, peak width, and the like). In some embodiments, one or more qualification and/or detection routines, e.g., as further described in Applicant's copending U.S. application Ser. No. 14/920,665, may be used to facilitate detection of samples including elevated EMG signal over background. Therein, a more detailed description of detection approaches for detecting samples of EMG signal data including elevated amplitude may be found.

In some embodiments, as shown in a step 44, a window of time (or clonic window) may be selected or determined. Generally, a clonic window may serve to organize results so that sample data or qualified sample data most useful to caregivers may be efficiently organized. In addition, in some embodiments, a clonic window may serve the purpose of organizing sample data so that it may operate most effectively or most effectively with respect to other routines used in an overall strategy of seizure monitoring, particularly as applied in real-time detection methods. For example, in some embodiments, when executed in a gated or intermittent manner, a sample detection routine may be configured with thresholds suitable to make sensitivity for sample detection high. For example, in some embodiments where sample detection is gated or where clonic windows are defined by other communicating routines (as shown by arrow 54), thresholds for sample detection may be set to improve sensitivity for sample detection. For example, levels of sensitivity may be used that would otherwise increase a rate of inadvertent sample detections (e.g., detection of samples unrelated to seizure sources) to levels that may be too high to be effectively used in generation of valid statistics representative of samples of seizure significance. However, when executed in a gated manner or based on definition of clonic windows as described in some embodiments herein, such concerns may be alleviated. Thus, in some embodiments, when executed in a gated manner or in a manner where only certain responses may be initiated based on samples within a clonic window, method 40 may operate efficiently.

A clonic window may include a start time and an end time, and may select a time period for determining various statistical metrics of EMG data. For example, the clonic window may define a period associated with the clonic phase of a seizure or other events that may produce signal patterns similar to those produced during a clonic-phase episode. In some embodiments, a clonic window may be determined using information provided in one or more seizure-detection routines. For example, in some embodiments, as shown by arrow 54, a response initiated by one of the seizure-detection routines (10, 20) may set a start time for a clonic window.

For example, in some embodiments wherein a start time for a clonic window is based off input from a routine 20, the start time for the clonic window may be based on a time in which a detection ratio determined from data collected in one or more epoch periods exceeds a detection ratio threshold. In some embodiments, the start time for a clonic window may be based on detection of samples of elevated signal amplitude. For example, a routine for detection of the presence of samples of elevated signal amplitude may run continuously or periodically. And, for example, only when some critical number of samples is detected may the start of a clonic window be initiated.

A clonic window may include an end time. In some embodiments, the end time for a clonic window may be a time that is some predetermined duration after a start time. For example, a window may last for about 10 seconds, about 15 seconds, about 20 seconds, about 30 seconds or some other suitable duration after the start time of the clonic window.

In some embodiments, an end time for the clonic window may be determined based on information obtained in another routine, including, for example, the method 20. For example, in the method 20, a seizure end flag detection may sometimes be issued when detection ratios calculated in all epoch periods in an 8-period window (or other suitable window) fall below a threshold. In other embodiments, an end flag detection may be issued based on an absence of detection of samples that may include elevations of signal amplitude. For example, if a suitable period of time progresses without identification of such samples, it may be deemed that the clonic phase of a seizure has progressed to completion and an end time for the clonic window may be established.

In some embodiments, samples of EMG signal including elevated amplitude over background may be detected and qualified against one or more criteria or thresholds suitable to identify that the samples may properly be associated with clonic-phase seizure activity. Sample qualification is further described, for example, in Applicant's copending U.S. application Ser. No. 14/920,665 wholly incorporated herein by reference. And, in some embodiments, in a step 46, samples of EMG signal including elevated signal amplitude over background detected in step 42 and defined within a clonic window established in step 44 may be qualified to be qualified-clonic-phase bursts. Statistical analysis of properties of samples of EMG signal including elevated amplitude over background or qualified-clonic-phase bursts may then be determined.

For example, in a step 46, various statistical values related to the clonic phase of a seizure may be determined. For example, a group of all identified samples and/or all qualified-clonic-phase bursts detected in a clonic window may be included in the statistical analysis included in the step 46. Generally, any property value of individual samples or qualified-clonic-phase bursts as described in the references incorporated herein may be determined in the step 46. By way of nonlimiting example, properties of samples (which may sometimes be qualified-clonic-phase bursts) may include duration width of sample elevated portions, duration width of an adjacent quiet period of a sample, total sample duration width, signal-to-noise, amplitude, and combinations thereof. Other properties related to groups of samples (which may sometimes be groups of qualified-clonic-phase bursts) may include a variation in duration of times between samples, sample repetition rate, regularity of one or more characteristics of samples, and/or combinations thereof. Any combination of those properties may be determined based on samples present in the clonic window, and various metrics including, for example, average, mean, median, standard deviation, percentage deviation or other statistical metrics and combinations thereof.

In some embodiments, the values of various properties of samples or qualified-clonic-phase bursts may be tracked over time within a clonic window. For example, trends in sample properties over time may be analyzed by executing a linear fit or curve fit of data across the clonic window. For example, in some embodiments, the time between elevated portions of samples detected in the clonic window may be included in a linear fit (or other suitable curve fit) to gather statistics about a detected event. Any of various times may be used to time stamp a sample or an elevated portion of a sample. For example, a leading edge of an elevation, trailing edge of an elevation, or any characteristic time within an elevated portion of a sample may be used as a time stamp.

Statistical values calculated in the step 46 may be organized in a summary of seizure information that may be provided to caregivers.

In a step 48, EMG signal data may be evaluated for characteristics of seizure activity and one or more responses may be initiated. For example, in some embodiments of the method 40, one or more of the seizure detection routines associated with box 50 (e.g., either or both of routines 10, 20) may detect a seizure during monitoring. Moreover, other routines may be executed in the method 40, including, for example, some of which may be sensitive to tonic or early parts of the clonic phase of a generalized tonic-clonic seizure. Thus, it should be understood that for many situations, when a clonic window ends, one or more alarms or other system responses based on detection of seizure activity may have already issued.

In some embodiments, one or more statistical values determined in step 46 may be evaluated in step 48 in order to better characterize the state of a patient. For example, if upon analysis of statistical data determined in step 46 a seizure suspected to be present is not confirmed, then it may be deemed that the detection was a false positive event. Accordingly, a caregiver or alarm response may be updated or cancelled.

For example, in some embodiments, the slope of a trend line for times between elevated portions of samples versus time in a clonic window may be compared to a threshold slope in order to characterize a seizure. Alternatively, as in Examples 1 and 2 below, the slope of a trend line for times between elevated portions of samples versus detected sample number in a clonic window may be compared to a threshold slope in order to characterize a seizure. In some embodiments, if the slope is greater than a threshold slope of about 1.0, for example, a seizure may be characterized as indicative of clonic phase activity typically associated with a patient having epilepsy. In some embodiments, a slope greater than about 1.5, greater than about 2.0, or greater than about 5.0, for example, may be used to characterize clonic phase activity typically associated with a patient having epilepsy.

In some embodiments, if the slope is less than a threshold slope of about 1.0, for example, a seizure may be characterized as indicative of activity typically associated with a patient having a condition other than epilepsy. Alternatively, as in Examples 1 and 2, the slope of a trend line for times between elevated portions of samples versus detected sample number in a clonic window may be compared to a threshold slope in order to characterize a seizure. In some embodiments, a slope less than about 0.8, for example, may be used to characterize activity typically associated with a patient having a condition other than epilepsy. For example, such activity may be indicative of a nonepileptic psychogenic seizure.

Generally, the devices of a seizure detection system may be of any suitable type and configuration to accomplish one or more of the methods and goals disclosed herein. For example, a server may comprise one or more computers or programs that respond to commands or requests from one or more other computers or programs, or clients. The client devices may comprise one or more computers or programs that issue commands or requests for service provided by one or more other computers or programs, or servers. The various devices for performing steps may be servers or clients depending on their function and configuration. Servers and/or clients may variously be or reside on, for example, mainframe computers, desktop computers, PDAs, smartphones, tablet computers, netbooks, portable computers, portable media players with network communication capabilities, cameras with network communication capabilities, smartwatches, wearable computers, wearable sensors, and the like.

A computer may be any device capable of accepting input, processing the input according to a program, and producing output. A computer may comprise, for example, a processor, memory and network connection capability. Computers may be of a variety of classes, such as supercomputers, mainframes, workstations, microcomputers, PDAs and smartphones, according to the computer's size, speed, cost and abilities. Computers may be stationary or portable, and may be programmed for a variety of functions, such as cellular telephony, media recordation and playback, data transfer, web browsing, data processing, data query, process automation, video conferencing, artificial intelligence, and much more.

A program may comprise any sequence of instructions, such as an algorithm, whether in a form that can be executed by a computer (object code), in a form that can be read by humans (source code), or otherwise. A program may comprise or call one or more data structures and variables. A program may be embodied in hardware or software, or a combination thereof. A program may be created using any suitable programming or scripting language, such as C, C++, Java, Perl, PHP, Ruby, SQL, and others. Computer software may comprise one or more programs and related data. Examples of computer software include system software (such as operating system software, device drivers and utilities), middleware (such as web servers, data access software and enterprise messaging software), application software (such as databases, video games and media players), firmware (such as device specific software installed on calculators, keyboards and mobile phones), and programming tools (such as debuggers, compilers and text editors).

Memory may comprise any computer-readable medium in which information can be temporarily or permanently stored and retrieved. Examples of memory include various types of RAM and ROM, such as SRAM, DRAM, Z-RAM, flash, optical disks, magnetic tape, punch cards, and EEPROM. Memory may be virtualized, and may be provided in or across one or more devices and/or geographic locations, such as RAID technology. An I/O device may comprise any hardware that can be used to provide information to and/or receive information from a computer. Exemplary I/O devices include disk drives, keyboards, video display screens, mouse pointers, printers, card readers, scanners (such as barcode, fingerprint, iris, QR code, and other types of scanners), RFID devices, tape drives, touch screens, cameras, movement sensors, network cards, storage devices, microphones, audio speakers, styli and transducers, and associated interfaces and drivers.

A network may comprise a cellular network, the Internet, intranet, local area network (LAN), wide area network (WAN), Metropolitan Area Network (MAN), other types of area networks, cable television network, satellite network, telephone network, public networks, private networks, wired or wireless networks, virtual, switched, routed, fully connected, and any combination and subnetwork thereof. The network may use a variety of network devices, such as routers, bridges, switches, hubs, repeaters, converters, receivers, proxies, firewalls, translators and the like. Network connections may be wired or wireless, and may use multiplexers, network interface cards, modems, IDSN terminal adapters, line drivers, and the like. The network may comprise any suitable topology, such as point-to-point, bus, star, tree, mesh, ring and any combination or hybrid thereof.

Wireless technology may take many forms such as person-to-person wireless, person-to-stationary receiving device, person-to-a-remote alerting device using one or more of the available wireless technologies such as ISM band devices, WiFi, Bluetooth, cell phone SMS, cellular (CDMA2000, WCDMA, etc.), WiMAX, WLAN, and the like.

Communication in and among computers, I/O devices and network devices may be accomplished using a variety of protocols. Protocols may include, for example, signaling, error detection and correction, data formatting and address mapping. For example, protocols may be provided according to the seven-layer Open Systems Interconnection model (OSI model), or the TCP/IP model.

Additional information related to the methods and apparatus described herein may be understood in connection with the examples provided below.

Example 1

Figure 4:
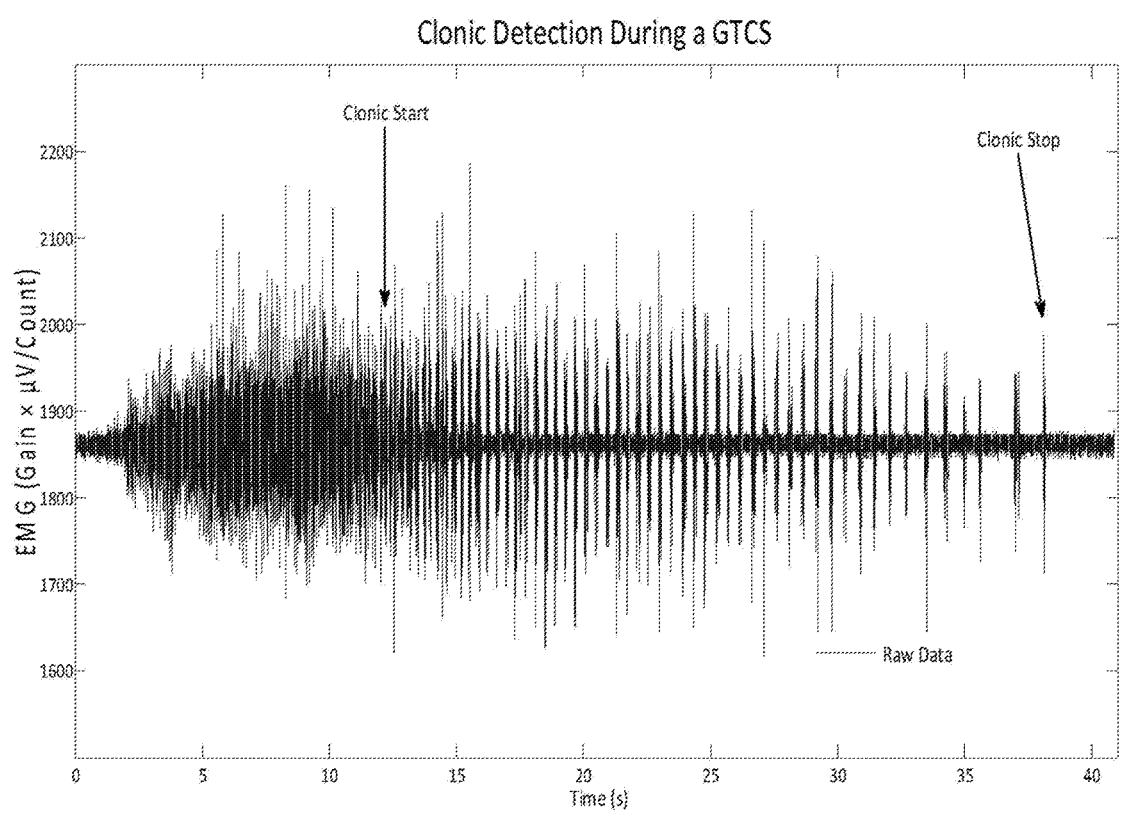
FIG. 4 illustrates EMG data for a patient showing a seizure event.
Figure 5:
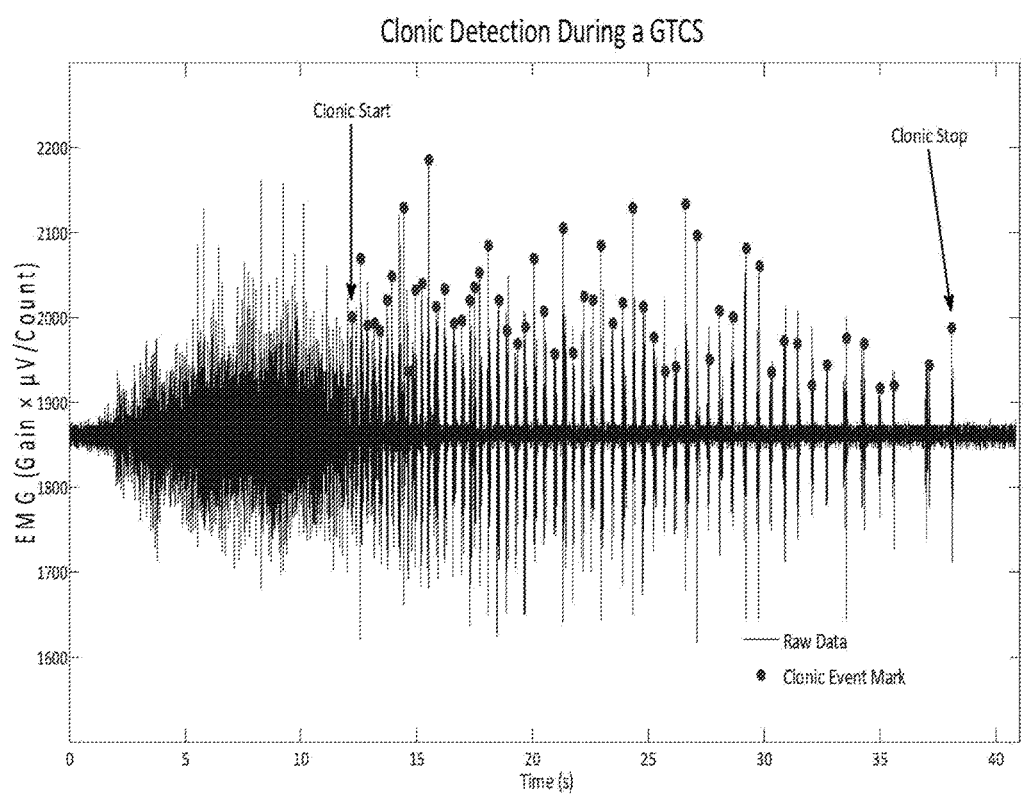
FIG. 5 illustrates the EMG data of FIG. 4 and includes markings showing positions where elevated portions of signal were identified in a detection window.
Figure 6:
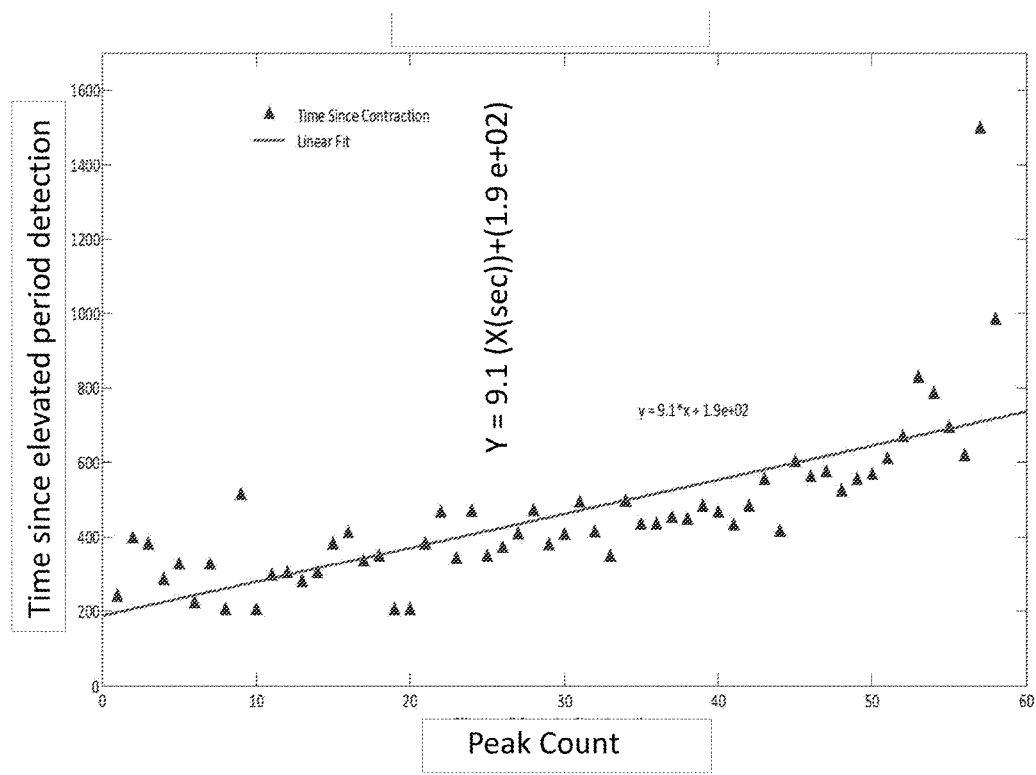
FIG. 6 illustrates a linear fit to data collected and shown in FIG. 5.
Figure 7A:
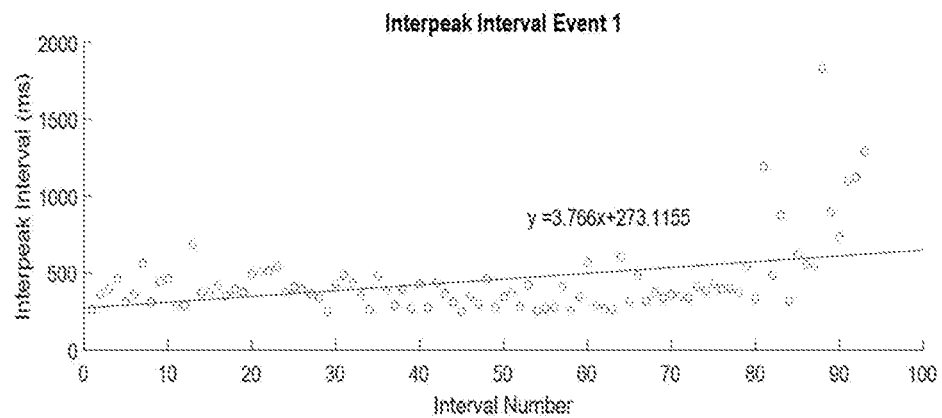
FIGS. 7A, 7B, 7C, 7D, and 7E illustrate results of regression analysis on EMG data for a GTC seizure.
Figure 7B:
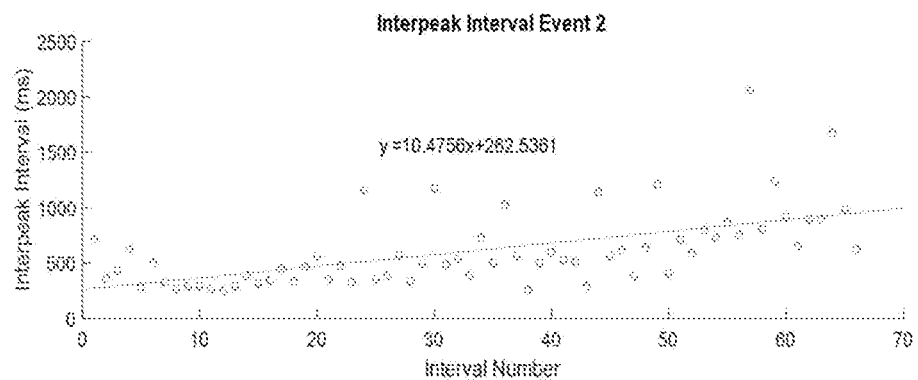
Figure 7C:
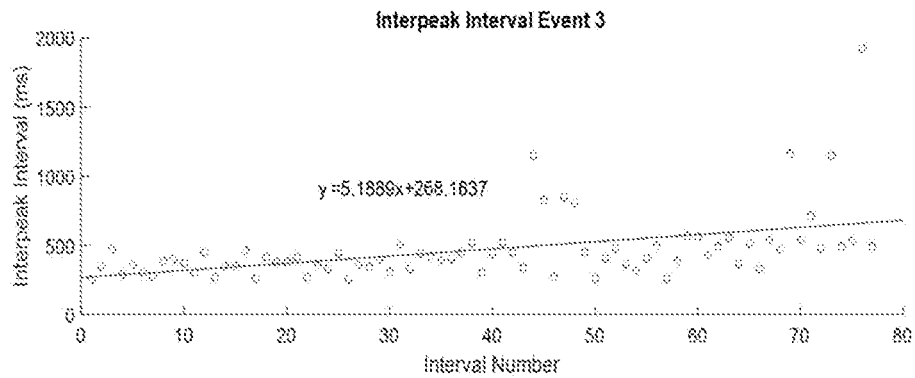
Figure 7D:
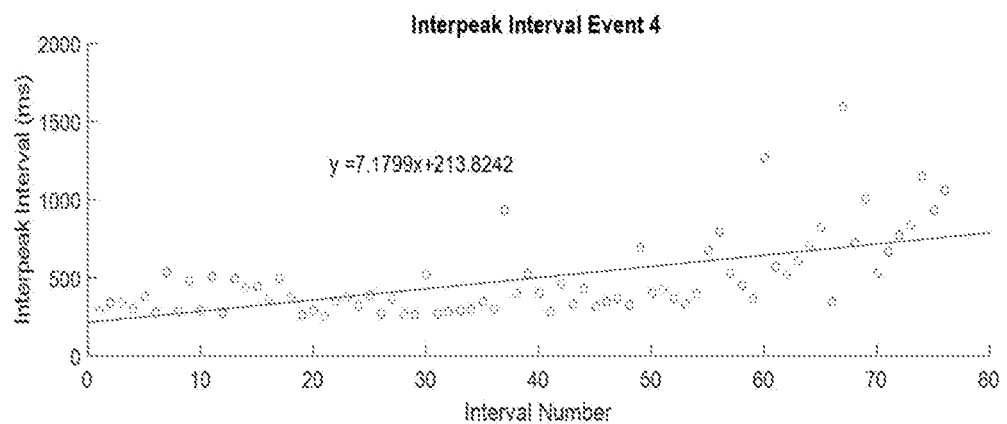
Figure 7E:
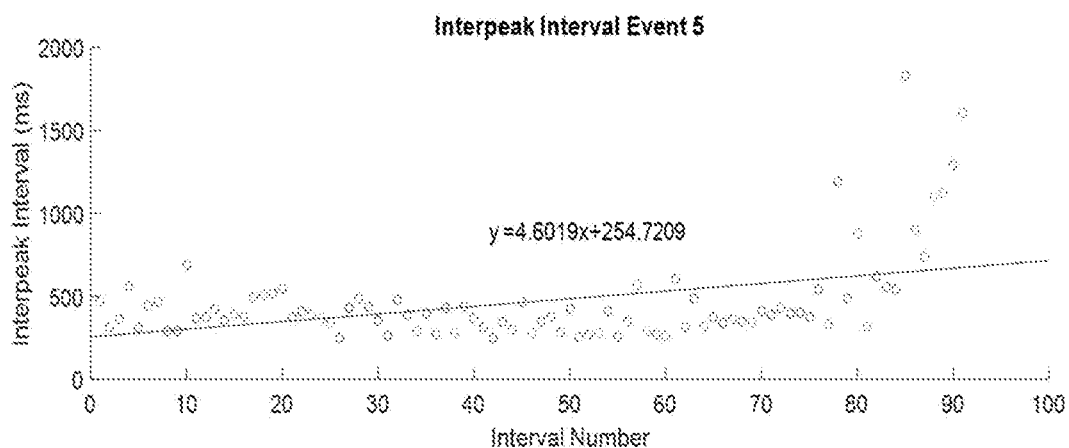

In this Example 1, a patient susceptible to seizures was monitored for seizure activity using EMG electrodes. A sensor was placed on the patient's biceps, EMG signal collected, the collected signal analyzed for the presence of seizure activity, and a seizure was detected. FIG. 4 shows EMG signal data for the patient. A peak detection algorithm was executed on the EMG data shown in FIG. 4. FIG. 5 marks various elevated signal portions identified in the EMG data and within the start and end times of a clonic detection window. The time between elevated portions of samples identified in the clonic phase was plotted against a detected interval number of samples detected and input into a linear least squared regression analysis. A result of that linear fit is shown in FIG. 6. As shown therein, the slope determined from the data in Example 1 is positive and statistically significant. That behavior is characteristic of an epileptic seizure and may be used to corroborate a finding that the patient seizure included a clonic phase.

Example 2

Figure 8:
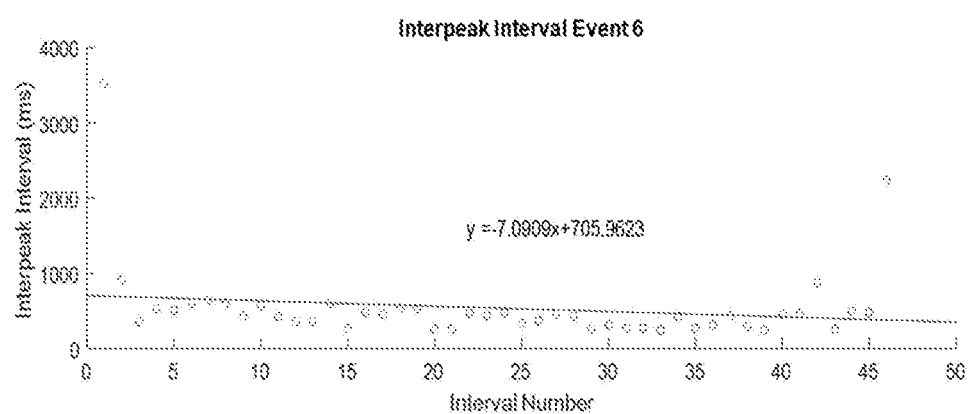
FIG. 8 illustrates results of regression analysis on EMG data for a psychogenic seizure event.

In this Example 2, referring to FIGS. 7A, 7B, 7C, 7D and 7E, the results of post-processing a number of detected seizures are shown. Particularly, five detected generalized tonic clonic (GTC) seizures and one detected psychogenic nonepileptic seizures are shown. The time between elevated portions of samples identified in the clonic phase was plotted against a detected interval number for samples detected. A linear least squares regression analysis was performed on data for each of the six detected events. The results of the regression analysis on events positively identified as GTC seizures are shown in FIGS. 7A, 7B, 7C, 7D and 7E. All events showed a positive and statistically significant slope. For the case of the detected psychogenic nonepileptic seizure, as shown in FIG. 8, regression analysis showed a slope that was negative.

Although the method and apparatus disclosed herein and their advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition, or matter, means, methods and steps described in the specification. For example, any feature described for one embodiment may be used in any other embodiment. Use of the word "include," for example, should be interpreted as the word "comprising" would be, i.e., as open-ended. As one will readily appreciate from the disclosure, processes, machines, manufactures, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufactures, compositions of matter, means, methods or steps.

What is claimed is:

1. A method of monitoring a patient for seizure activity comprising:
    collecting an electromyography signal using one or more electromyography electrodes;
    sending the electromyography signal to a processor;
    processing with the processor the collected electromyography signal to identify when the electromyography signal includes elevations in signal amplitude;
    analyzing with the processor whether times between said elevations in signal amplitude within a clonic window change in a manner indicative of a non-epileptic psychogenic event;
    said analyzing includes determining a linear fit for how said times between said elevations in signal amplitude change over time, obtaining a slope from said linear fit, and determining that the times between said elevations are indicative of a non-epileptic psychogenic event in response to the slope being less than the maximum threshold value; and
    reporting the non-epileptic psychogenic event to a caregiver in the event that said non-epileptic psychogenic event is identified.

2. The method of claim 1 wherein said maximum threshold value is about 0.8.

3. The method of claim 1 wherein said clonic window includes a start time determined using one or more seizure-detection routines.

4. The method of claim 1 wherein said clonic window includes a start time determined using one or more seizure-detection routines; and
    wherein at least one of said one or more seizure-detection routines is configured to detect one or more times near the start of a clonic phase of a seizure.

5. The method of claim 1 wherein said clonic window includes a start time and an end time, each of said start time and said end time is determined using one or more seizure-detection routines; and
    wherein at least one of said one or more seizure-detection routines is configured to detect one or more times near the start of a clonic phase of a seizure.

6. The method of claim 1, further comprising:
    analyzing whether the times between said elevations in signal amplitude within said clonic window change in a manner indicative of an epileptic seizure; and
    reporting an epileptic seizure to a caregiver in response to the times between said elevations changing in a manner indicative of the epileptic seizure.

7. The method of claim 6 wherein said clonic window includes a start time determined using one or more seizure-detection routines.

8. The method of claim 6 wherein said clonic window includes a start time determined using one or more seizure-detection routines; and
    wherein at least one of said one or more seizure-detection routines is configured to detect one or more times near the start of a clonic phase of a seizure.

9. The method of claim 6 wherein said clonic window includes a start time and an end time, each of said start time and said end time determined using one or more seizure-detection routines; and
    wherein at least one of said one or more seizure-detection routines is configured to detect one or more times near the start of a clonic phase of a seizure.

10. A method of monitoring a patient for seizure activity comprising:

processing with a processor electromyography signal data to identify when the electromyography signal data includes elevations in signal amplitude;

analyzing with the processor whether times between said elevations in signal amplitude within a clonic window change in a manner indicative of a non-epileptic psychogenic event;

said analyzing includes determining a linear fit for how said times between said elevations in signal amplitude change over time, obtaining a slope from said linear fit, and determining that the times between said elevations are indicative of a non-epileptic psychogenic event in response to the slope being less than the maximum threshold value; and reporting the non-epileptic psychogenic event to a caregiver in the event that said non-epileptic psychogenic event is identified.

11. A computer including a processor programmed with instructions for executing a method for analyzing a collected electromyography signal for non-epileptic psychogenic events, the method comprising:

processing with the processor the collected electromyography signal to identify when the electromyography signal includes elevations in signal amplitude;

analyzing with the processor whether times between said elevations in signal amplitude within a clonic window change in a manner indicative of a non-epileptic psychogenic event by determining a linear fit for how said times between said elevations in signal amplitude change over time, obtaining a slope from said linear fit, and determining that the times between said elevations are indicative of a non-epileptic psychogenic event in response to the slope being less than the maximum threshold value; and reporting the non-epileptic psychogenic event to a caregiver in the event that said non-epileptic psychogenic event is identified.

12. The computer of claim 11, the method further comprising determining if said slope is above a minimum threshold value.

13. The computer of claim 11, the method further comprising determining a start time for said clonic window using one or more seizure detection routines configured to detect one or more times near the start of a clonic phase of a seizure.

* * * * *